United States Patent [19]
Garfield et al.

[11] Patent Number: 5,595,970
[45] Date of Patent: Jan. 21, 1997

[54] TREATMENT OF CLIMACTERIC DISORDERS WITH NITRIC OXIDE SYNTHASE SUBSTRATES AND/OR DONORS

[75] Inventors: Robert E. Garfield, Friendswood, Tex.; Krzysztof Chwalisz; Radoslaw Bukowski, both of Berlin, Germany; Chandra Yallampalli, Houston, Tex.

[73] Assignee: Schering Aktiengesellschaft, Berlin, Germany

[21] Appl. No.: 153,345

[22] Filed: Nov. 16, 1993

Related U.S. Application Data

[63] Continuation-in-part of Ser. No. 92,426, Jul. 16, 1993, abandoned.

[51] Int. Cl.⁶ .......................... A61K 31/04; A61K 31/56; A61K 31/155
[52] U.S. Cl. .............................. 514/12; 514/21; 514/171; 514/412; 514/561
[58] Field of Search .............................. 514/12, 21, 412, 514/561, 171

[56] References Cited

FOREIGN PATENT DOCUMENTS

WO95/22345  8/1995  WIPO.

OTHER PUBLICATIONS

Bayhi et al., J. Clin. Anesth., 4:487–488 (1992).
Conrad. FASEB. 7:566–571 (1993).
Diamond, J. of Pharm. & Exp. Thera., 168(1):21–30 (1969).
Garfield et al., "Control of Myometrial Contractility and Labor," *Basic Mechanisms Controlling Term and Preterm Labor*, Springer–Verlag Berlin, eds. Chwalisz et al. (1994).
Greenspoon et al., Lancet, 338:124 (1991).
Izumi et al., Am. J. Obstet. Gynecol., 170:236–245 (1994).
Jennings et al., J. of Mat. Fetal Med., 2:170–174 (1993).
Lees et al., Lancet, 343:1325–1326 (1994).
Natuzzi et al., Biochem. & Biophys. Res. Comm., 194(1):1–8 (1993).
Papka et al., Neuroscience Letters, 147:224–228 (1992).
Ramsey et al., Europ. J. of Clinical Investigation, 24:76–78 (1994).
Sladek et al., Endocrinology, 133(4):1899–1904 (1993).
Yallampalli et al., Am. J. Obstet, Gynecol., 169:1316–1320 (1993).
Yallampalli et al., Am. J. Obstet, Gynecol., 169:1285–1291 (1993).
Yallampalli et al., Am. J. Obstet. Gynecol., 170:175–185 (1993).
Yallampalli et al., Endocrinology, 134(4):1971 (1994).
Braz J. Med. Biol. Res. vol. 26 No 8, (1993) pp. 853–857) Chaves et al "Possible involvement of nitric oxide in estrogen–induced uterine edema in the immature rat."
Loscalzo et al WO9218002 Oct. 29, 1992 APS Abstract.
Yallampalli et al., Soc. Gynecol. Invest. Abst. P41 (1993).

*Primary Examiner*—Herbert J. Lilling
*Attorney, Agent, or Firm*—Millen, White, Zelano & Branigan, P.C.

[57] ABSTRACT

The symptoms of the climacterium are ameliorated by the administration to an afflicted individual one or both of a nitric oxide substrate and/or nitric acid donor, alone or optionally in combination with a progestin or, in the case of a non-pregnant female, either a progestin or an estrogen or both.

14 Claims, 2 Drawing Sheets

TREATMENT OF CLIMACTERIC DISORDERS WITH NITRIC OXIDE SYNTHASE SUBSTRATES AND/OR DONORS

This application is a continuation-in-part of Ser. No. 08/092,426 filed 16 Jul. 1993 now abandoned.

BACKGROUND OF THE INVENTION

This invention relates to a method for the treatment and prevention during menopause of climacteric disorders such as hot flushes, abnormal clotting patterns, urogenital discomfort, increased incidence of cardiovascular diseases, etc., associated with the reduction in ovarian function in middle-aged women, with a nitric oxide synthase substrate (L-arginine), a nitric oxide donor or both, alone or (in the case of females) in combination with estrogen and/or progestin hormone replacement therapy (HRT) or, in the case of males, in combination with a progestin.

It is now well known that HRT, such as estrogen treatment, improves or reverses the adverse effects of the versation of sex steroid secretion by the ovaries during menopause. Estrogens have also been shown to improve mood and psychological well-being in postmenopausal women and they also prevent atrophic changes in the genital tract. Estrogens have been shown to effect arterial tone and this may help to explain the reduction in hot flushes observed in postmenopausal women with estrogen therapy. On the other hand, unopposed estrogen therapy has been associated with endometrial hyperplasia and endometrial cancer.

Many studies have shown that the addition of progesterone to estrogen HRT decreases the risk of endometrial cancer and even reverses endometrial hyperplasia. However, progestins are not without their own untoward side effects.

Progestins may oppose the beneficial effects of estrogens on the cardiovascular system by inducing an atherogenic profile in plasma lipids. Moreover, persistent irregular or withdrawal bleedings are common with continuous or sequentially combined estrogen-progestin therapy. In any event, modern HRT now employs combinations of an estrogen and a progestin as in the general case for most contraceptives.

One of the most exciting recent advances in biology and medicine is the discovery that nitric oxide is produced by endothelial cells and that it is involved in the regulation of vascular tone, platelet aggregation, neurotransmission and immune activation (Furchgott and Zawadzki, 1980; Moncada, Palmer and Higgs, 1991; Ignarro, 1991). Nitric oxide is an important mediator of relaxation of the muscular smooth muscle (Montada, Palmer and Higgs, 1991) and was formerly known as EDRF (endothelin-derived relaxing factor) (Furchgott und Zawadzki, 1980; Moncada, Palmer and Higgs, 1991). Nitric oxide is synthesized by the oxidative deamination of a guanidino nitrogen of L-arginine by at least different isoforms of a flavin-containing enzyme, nitric oxide synthase (Montada, Palmer and Higgs, 1991). Synthesis of nitric oxide has been shown to be competitively inhibited by analogues of L-arginine; NG-nitro-L-arginine methyl ester (L-NAME), NG-monoethyl-L-arginine (LMMA), N-iminoethyl-L-arnithine (L-NIO), L-monomethyl-L-arginine (L-NNMA) and L-NG-methylarginine (LNMA) and Nw-nitro-L-arginine (L-NA).

Nitric oxide elevates levels of cGMP (1,3,5-cyclic guanosine monophosphate) within the vascular smooth muscle to produce relaxation and to reduce blood vessel tone (Moncada, Palmer and Higgs, 1991). Nitric oxide binds to heme and thus activates soluble guanylate cyclase (Ignarro, 1991) to increase the cellular content of cGMP. It has long been recognized that nitrovasodilators, such as nitroprusside and nitroglycerin, inhibit vascular smooth muscle contractility to produce relaxation or to reduce vascular tone. These agents have been used since the late 1800's as vasodilators. However, only recently has the mechanism of action of these compounds been realized. Nitrovasodilators are now classified as nitric oxide donors because they are metabolized to release nitric oxide (Moncada, Palmer and Higgs, 1991). The long-used nitrovasodilators may be regarded as substitution therapy for a failing physiological mechanism. Nitric oxide is also produced by macrophages and other immune cells.

There is a substantial body of evidence from animal experiments that a deficiency in nitric oxide contributes to the pathogenesis of a number of diseases, including hypertension, atherosclerosis and diabetes (Montada, Palmer and Higgs, 1991). There are many recent studies showing that the inhibition of nitric oxide synthase dramatically increases blood pressure. The inhibition of nitric oxide synthesis with L-NNMA, L-NA or L-NAME causes long-lasting elevation in blood pressure and suggests that its reduction may contribute to the pathogenesis of hypertension (Moncada and Palmer, 1992). Furthermore, L-NAME-treatment potentiates pressor responses to angiotensin II, vasopressin and norepinephrine. Also, in patients with pregnancy-induced hypertension, release of nitric oxide by umbilical vessels is blunted (Pinto et al, 1991) and the physiological decrease in blood pressure in pregnant spontaneous hypertensive rats was shown to depend on endothelial nitric oxide (Ahokas, Merces and Sibai, 1991). Additionally, infusion of L-NA increases blood-pressure in pregnant rats and potentiates responses to vasopressors (Molnar and Hertelendy, 1992). These studies suggest that impaired nitric oxide synthesis may be an important mechanism in the etiology of cardiovascular problems.

Nitric oxide synthesis and nitric oxide effector system (cGMP-dependent relaxation mechanism) are thought to be regulated by steroid hormones. There is an increase in cardiovascular diseases in women following menopause and which may be related to the decrease in sex steroids and an alteration in nitric oxide. Female steroid hormones have been shown to modulate endothelium-dependent relaxation of vascular smooth muscle by nitric oxide. Estradiol treatment of rats causes increased nitric oxide production by vascular tissues, whereas progesterone counteracts this phenomenon (Miller and Van Houtte, 1991). It is well known that pregnancy is associated with an increase in cardiac output and a decrease in the resistance of virtually all the vascular beds in the body. Although the mechanism of this phenomenon is not known, it could be associated with changes in nitric oxide production or effects as a result of elevated steroid hormone levels. One important observation with regard to the above mechanism is that antiprogestins (RU 486) elevate blood pressure in animals (Kalimi, 1989) and they produce hot flushes in humans, both males (Grunberg et al., 1993) and females (Kettel et al., 1991). The hot flushes may be mediated by the steroid action on the release of nitric oxide. Hot flushes are a primary symptom in menopausal, postmenopausal women and they are relieved by both estrogen and progesterone (Avis et al., 1993).

The studies described below show that nitric oxide and the subsequent relaxation of the uterus is controlled by progesterone. The relaxation effects of the nitric oxide substrate, L-arginine, are greater in late pregnancy when progesterone levels are elevated in pregnant rats. Also there is greater uterine relaxation with L-arginine when uterine strips are taken from nonpregnant, ovariectomized rats treated with progesterone. In addition, treatment with pregnant rats with the nitric oxide inhibitor produces signs and symptoms of preeclampsia (e.g., hypertension, fetal retardation and proteinurea—the classical triad of preeclampsia). These symptoms are related to the decrease in vascular resistance and placental perfusion. Preeclampsia is a well known model of atherosclerosis as the decrease in placental perfusion is accompanied by increased fibrin deposition in placental vessels and increased thrombus formation (Roberts et al., 1989). Thus, nitric oxide substrates and/or donors alone or in combination with estrogen and progesterone will be particularly efficacious for hormone replacement therapy to prevent climacteric symptoms (climacterium) such as atherosclerosis, hypertension, hot flushes, etc.

EP 0441 119 A2 discloses the use of L-arginine in the treatment of hypertension and other vascular disorders. It suggests that the mechanism by which L-arginine is effective for this purpose is because it may be the physiological precursor of "the most powerful endothelial-derived releasing factor, nitric oxide." The use of L-arginine in combination with other pharmaceutically active agents is not discussed in this publication.

OBJECTS OF THE INVENTION

It is an object of the invention to provide a method for the prevention and treatment of climacterium (climacteric symptoms) with a nitric oxide substrate and/or donor in both male and in non-pregnant female mammals.

It is another object to provide such a method in which a progestational agent is used in combination with a nitric oxide substrate and/or donor for the prevention and treatment climacterium (climacteric symptoms) in both male and in non-pregnant female mammals.

It is a further object to provide a method for hormone replacement therapy (HRT) in non-pregnant peri- and in post-menopausal female mammals using a estrogenic agent in combination with a nitric oxide substrate and/or donor.

It is another object to provide a method for hormone replacement therapy (HRT) in non-pregnant peri- and in post-menopausal females using a combination of an estrogenic agent and progestational agent with a nitric oxide substrate and/or donor.

A further object is the provision of pharmaceutical compositions useful in practicing the methods of this invention.

Upon further study of the specification and appended claims, further objects and advantages of this invention will become apparent to those skilled in the art.

SUMMARY OF THE INVENTION

In a method aspect, this invention relates to a method of treating the climacterium symptoms in a non-pregnant female or in a male mammal which comprises administering to an individual manifesting the symptoms thereof one or both of a nitric oxide donor, alone or in further combination with a progestin, or, in the case of a female mammal, in further combination with one or both of a progestin and an estrogen, or in the case of a male mammal, in further combination with an androgen in amounts effective to ameliorate the symptoms thereof, the amount of the estrogen being bioequivalent to approximately 2 mg per day of estradiol (Progynova®, Schering), and the amount of the progestational agent administered being bioequivalent to 50–300 mg of injected progesterone and the amount of the nitric oxide synthase substrate, nitric oxide donor or both being effective to, respectively, either raise the blood level of circulating L-arginine in a pregnant female to whom the composition is administered to at least about 10–50 nmole above the normally 50–100 nmole circulating levels or raise nitric oxide donor levels to about 1–100 nmolar (nanomolar).

In a product aspect, this invention relates to a pharmaceutical composition comprising at least one of the nitric oxide synthase substrate and a nitric oxide donor, alone or in further combination with one or more of a estrogen and/or progestin with the amount of the estrogen being bioequivalent to about 2 mg of estradiol (e.g., Progynova®, Schering) with the amount of the estrogen being bioequivalent to 50–300 mg of injected progesterone and the amount of the nitric oxide synthase substrate, a nitric oxide donor or both per unit dosage being effective to, respectively, either raise the blood level of circulating L-arginine to at least about 10–50 nmole above the normally 50–100 nmolar circulating levels or raise the nitric oxide donor levels to about 1 to 1000 nmolar.

DETAILED DISCLOSURE

The methods of this invention treat climacterium (climacteric symptoms) in a menopausal/postmenopausal mammal, e.g., a nonpregnant female or in a male human, who is manifesting the symptoms thereof or who is a high risk candidate for doing so, e.g., based on rate of bone loss rate.

Because these abnormal conditions of menopause/postmenopause are produced by or aggravated by subnormal nitric oxide synthesis, both nitric oxide synthase substrates, e.g., L-arginine, and nitric oxide donors, e.g., sodium nitroprusside, nitroglycerin, glycerin trinitrate, SIN-1, isosorbid mononitrate and isosorbid dinitrate, are useful for ameliorating the symptoms thereof and, in one aspect of the method of this invention, a combination of both are employed.

An additive effect is achieved when a progestational agent is administered concurrently with the nitric oxide substrate and/or nitric acid donor. In the case of a female mammal, an estrogen can be administered concurrently with or in lieu of the progestin. In the case of a male mammal, an androgen can be administered concurrently with the progestin if the latter causes down regulation of testosterone levels, e.g., in amounts effective to raise blood serum total testosterone level to between about 100 and about 600 mg/dl.

Thus, the method aspect of this invention and the pharmaceutical composition aspect of this invention employs either or both of a nitric oxide donor and a nitric oxide synthase substrate and, optionally, one or more of a progestin (e.g., progesterone or norgestrel), or, in the case of a female mammal, both a progestin and an estrogen (e.g., Prygynova®, Schering).

Examples of dosage ranges of typical NO-substrates and NO-donors (per os) are:

| | total dose: |
|---|---|
| L-Arginine | 500 mg–10 g p.o. |
| Sodium Nitroprusside | range 500–2000 ug/kg/day |
| Nitroglycerin | 0.5–10 mg |
| Isosorbid mononitrate | 10–100 mg |
| Isosorbid dinitrate | 10–100 mg |

Examples of combinations of active agents which can be administered concurrently with a nitric oxide substrate and/ or nitric oxide donor are the following estrogens and progestins and typical oral dosage ranges active agents of the estrogen and progestin with the nitric oxide substrate or donor:

Estrogens: A daily dose bioequivalent to about 1 to 2 mg per day, e.g., Premarin®, Wyeth-Ayerst, 0.625 mg/day, estradiol valerate, 50 ug/day transdermally, vaginal estradiol creams, 1.25 mg/day and vaginal estradiol rings, 0.2 mg/day and the natural occurring oestrogens used in hormone replacement therapy currently available in the UK.

Progestins: A daily dose bioequivalent to 50–300 mg of progesterone/day, e.g., an injectable suspension of medroxyprogesterone acetate to provide a weekly dose of thereof of 100–1000 mg or tablets or dragees providing an oral dose thereof of 5–10 mg/day, an injectable solution of hydroxyprogesterone caproate which provides a weekly dose of 250–500 mg; tablets, capsules or dragees of northindrone acetate which provide a daily dose of 5–20 mg.

Examples of estrogen and progestin combinations are listed below:

| Product | Composition | Dose (mg per day) |
|---|---|---|
| Climaval ® (Sandoz) | Oestradiol valerate | 1 or 2 |
| Progynova ® (Schering) | Oestradiol valerate | 1 or 2 |
| Harmogen ® (Abbott) | Piperazine oestrone sulfate | 1.5 or 2.5 |
| Hormonin ® (Shire) | Oestradiol + Oestrone + Oestriol | 0.6 |
| Premarin ® (Wyeth-Ayerst) | Conjugated equine oestrogens | 0.625 or 1.25 or 2.5 mg. |

Commercially available combination calendar packs for hormone replacement therapy include "Estrapak", "Prempak-C", "Trisequens", "Trisequens forté" and "Cycloprogynova" The following are illustrative compositions of such products:
Oestradiol 50 mg per day (28 days, 8 patches) conjugated equine oestrogens 0.625 mg per day (28 days)
Oestradiol valerate 2 mg per day (11 days) Oestradiol valerate 2 mg per day Norgestrel 0.5 mg per day (10 days)
Norgestrel 0.15 mg per day (12 days) conjugated equine oestrogens 1.25 mg per day (28 days)
Norgestrel 0.15 mg per day (12 days) Oestradiol 2 mg per day+oestriol 1 mg per day (22 days)
Norethisterone acetate 1 mg per day (10 days) Oestradiol 1 mg per day+oestriol 0.5 mg per day (6 days) Oestradiol 4 mg per day+oestriol 2 mg per day (21 days)
Norethisterone acetate 1 mg per day (10 days) Oestradiol 1 mg per day+oestriol 0.5 mg per day (6 days) Oestradiol valerate 1 mg per day (21 days)
Levonorgestrel 0.25 mg per day (10 days) Oestradiol valerate 2 mg per day (21 days)
Levonorgestrel 0,5 mg per day (10 days)
Daily doses of progestogens taken for 12 days per month in patients receiving oral or transdermal oestrogens:

| Norethisterone | 0.7–2.5 mg per day |
|---|---|
| Medroxyprogesterone acetate | 10 mg per day |
| Norgestrel | 150 µg per day |
| Dydrogesterone | 10–20 mg per day |

The pharmacologically active agents employed in this invention can be administered in admixture with conventional excipients, i.e., pharmaceutically acceptable liquid, semi-liquid or solid organic or inorganic carriers suitable, e.g., for parental or enteral application and which do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, vicious paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories and transdermal patches. Ampoules are convenient unit dosages.

In a preferred aspect, the composition of this invention is adapted for ingestion.

For enteral application, particularly suitable are unit dosage forms, e.g., tablets, dragees or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coatings, etc.

Suitable for oral administration are, inter alia, tablets, dragees, capsules, pills, granules, suspensions and solutions. Each unit dose, e.g., each tablespoon of liquid or each tablet, or dragee contains, for example, 5–5000 mg of each active agent.

Solutions for parenteral administration contain, for example, 0.01–1% of each active agent in an aqueous or alcoholic solution.

The nitric oxide substrate and/or donor can be administered as an admixture with an estrogen and/or progestational agent and any other optional active agent or as a separate unit dosage form, either simultaneously therewith or at different times during the day from each other.

The combination of active agents is preferably administered at least once daily (unless administered in a dosage form which delivers the active agents continuously) and more preferably several times daily, e.g., in 2 to 6 divided doses. The typical dose is about 0.5 to 1000 mg of each active agent, although some less active agents, e.g., L-Arginine, require much higher oral dosages, e.g., 500 to 10,000 mg, and others, e.g., sodium nitroprusside, require lower doses, e.g., 500–2,000 ug/kg/day. Doses for nitroglycerine typically are orally 2.5 mg 2×daily; sublingually, 0.8 mg 1–4×daily; and transdermally, 0.2–0.4 mg/hr. Since the LD50 dosages of most of these active agents is known in the prior art, a lower dosage regimen can be initiated and the dosage increased until a positive effect is achieved or a higher dosage regimen can initially be employed, e.g., in a crisis situation, and the dosages regulated downward as relief from the symptoms is achieved. Combinations of agents can be employed either continuously or sequentially.

In humans, both L-arginine and progesterone (or bioequivalent of another progestin) should be given in a ratio which produces blood plasma levels of about 50–200 nmolar L-arginine, 30–100 nmolar progesterone and 500 to 1000 nmolar of estradiol.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
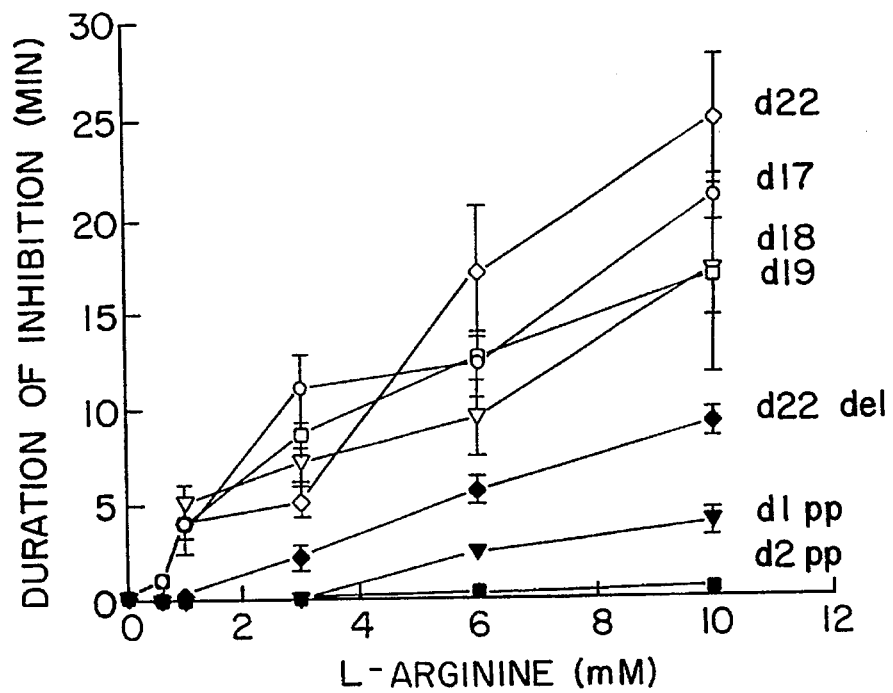
FIG. 1: Dose-dependent relaxation effects of L-arginine (0.1 mM to 10 mM) on spontaneously contracting uterine strips from rats at different stages of gestation, during delivery and post partum.

In the experiments whose results are shown by the graph of FIG. 1, the tissues were obtained on days 17–22 (d17, d18, d19 and d22) of gestation, on day 22 (d22 del) during spontaneous delivery (1–3 pups delivered), or on 1 (d1pp) and 2 (d2pp) days postpartum. The duration of complete inhibition of spontaneous uterine contractions are dose-dependent. The effects of L-arginine from concentrations of 1 mM are significantly ($p<0.01$) decreased during spontaneous delivery at term and postpartum, compared to all other times. Data are analyzed by repeated measures ANOVA on seven groups. Each data point represent mean+S.E.M. The total number of strips studied at each time period was 8–16 from 4–6 animals per group.

Figure 2:
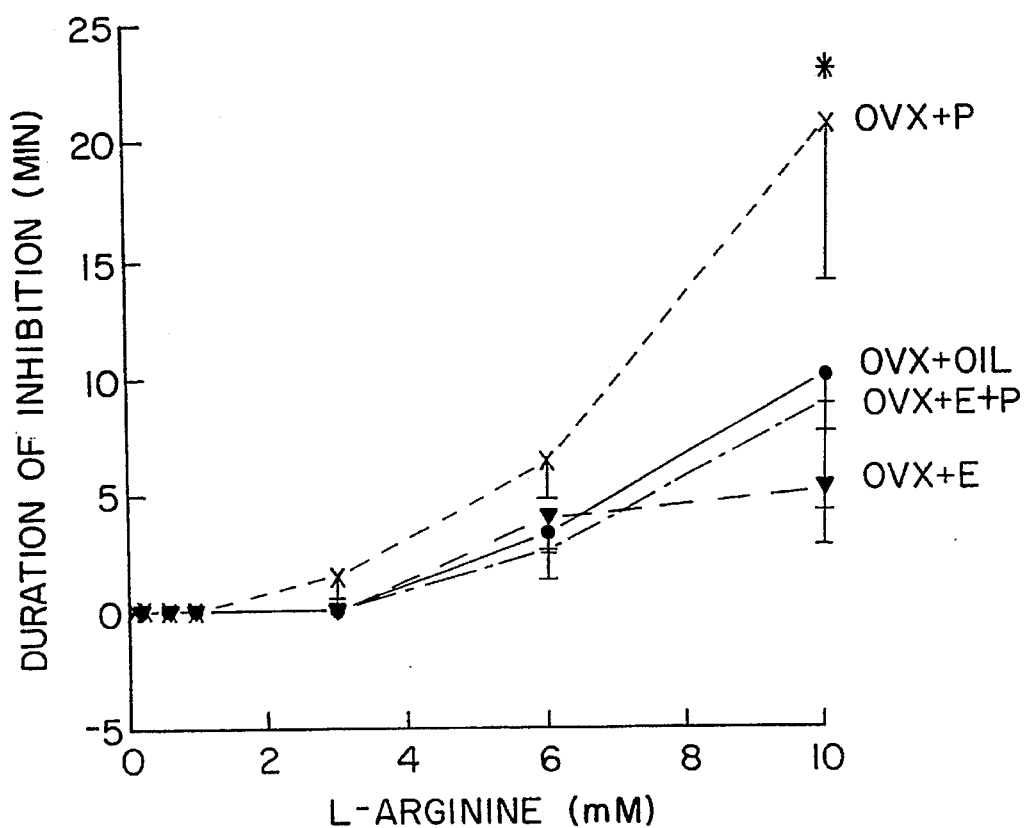
FIG. 2: Dose response effects of L-arginine (0.6 mM to 10 mM) on the spontaneous contractility of uterine strips from ovariectomized nonpregnant adult rats.

In the experiments whose results are shown by the graph of FIG. 2, nonpregnant, nonpregnant ovariectomized rats received s.c. injection of 1 ug estradiol-17-β (OVX+E), 2 mg progesterone (OVX+P), estradiol and progesterone (OVX+E+P) in sesame oil or oil alone (OVX and Oil) for 3 days prior to contractility measurements. Values are mean+SEM for 4 strips from each animal from 4 rats per group.

*$p<0.05$ OVX+p vs OVX+E.

Figure 3:
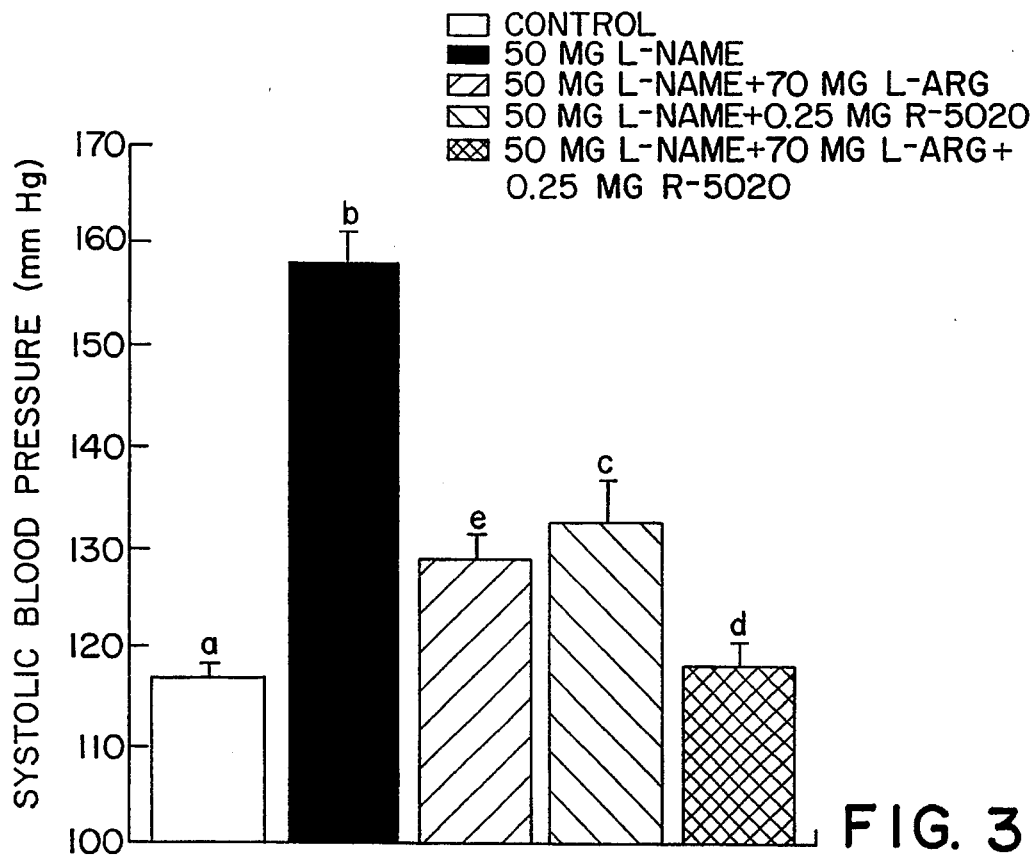
FIG. 3: is a bar chart which shows the effect on blood pressure of test animals (rats) after 50 mg of the nitric oxide inhibitor L-NAME, alone or in combination with one or both of L-arginine and a progestin promegestone, R5020.

The data in FIG. 3 show that L-NAME produced hypertension ("preeclampsia"). Treatment of animals with L-arginine alone partially reduced blood pressure induced with L-NAME. Similarly, animals treated with L-NAME and R5020 (promegestone), a progestational agent with no anti-mineralocorticoid effect or other antagonistic or agonistic properties, also partially reduced L-NAME-induced hypertension. As also shown in FIG. 3, when the same doses of L-arginine and R 5020 were given simultaneously, their combined effect lowered blood pressure to normal levels.

Figure 4:
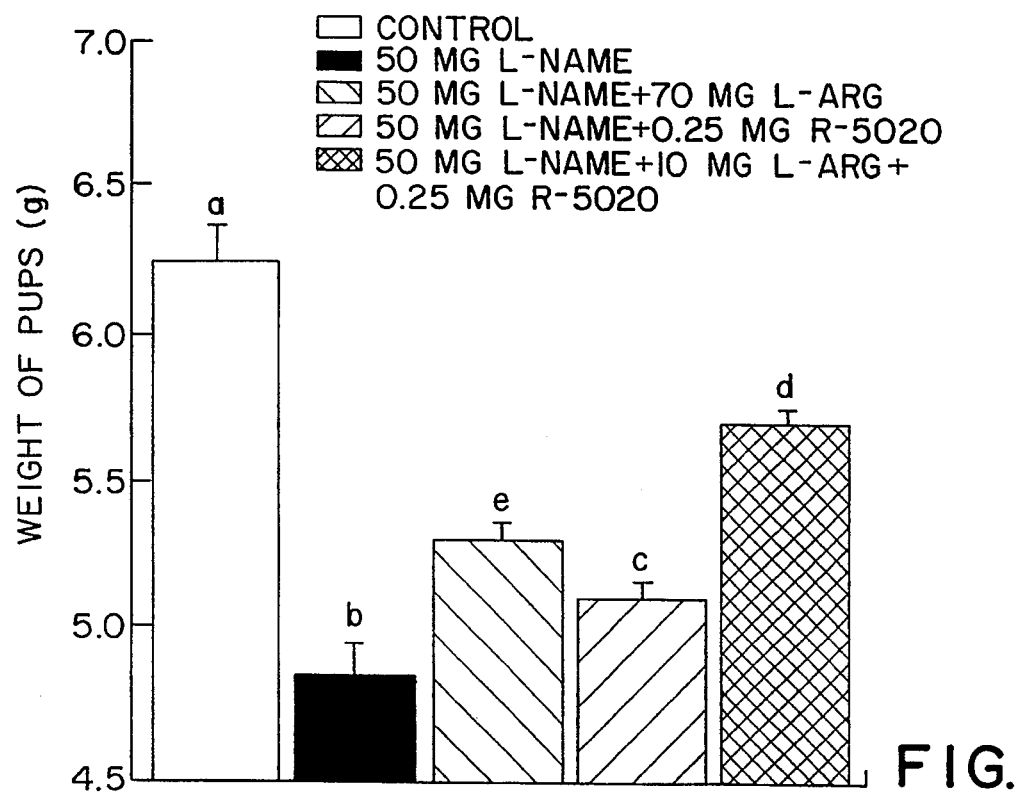
FIG. 4: is bar chart which shows the effect in the same experiments on pup weights of these compounds.

Additionally, evaluation of fetal weights in the same animals treated as described above, showed intrauterine fetal retardation (decreased weight of pups), typical preeclamptic fetuses (FIG. 4).

Treatment of the "preeclamptic" groups of animals with either L-arginine alone or R 5020 alone slightly but statistically significant, elevated fetal weights. As also shown in FIG. 6, the combined effect of the two compounds administered together significantly elevated fetal weight above that observed with either compound alone, a highly significant advantage to survival of the fetus under these conditions.

It can be concluded from these studies that the effects of L-arginine to relax the pregnant uterus are dependent upon progesterone. Further, since estrogen is required for progesterone actions, to induce progesterone receptors , it can be inferred that estrogen is important for the relaxation effects. L-arginine is a substrate for nitric oxide synthesis. Therefore, it can be concluded that nitric oxide effects are mediated by the steroid hormones. Further, the studies with intact pregnant rats show that the inhibition of nitric oxide synthesis with L-NAME significantly elevates blood pressure and reduces fetal weights. Both blood pressure and fetal weights are improved in L-NAME treated rats given a nitric oxide substrate (L-arginine) alone or in combination with progesterone (R-5020). Since nitric oxide is known to control atherosclerosis, L-NAME-treatment is identical with preeclampsia and this condition is associated with other sclerosis and atherosclerosis hypertension is accelerated in climacterium, treatment with nitric oxide substrates and/or nitric oxide donors alone or in combination with estrogens and progesterone will have tremendous advantages for climacterium therapy.

The method of treatment employed in this invention can also be employed for the treatment of hypertension (in both females and males), as an adjuvant in contraceptive therapy, thrombotic disorders, menstrual disorders (dysmenorrhea, functional uterine bleeding), and hemorrhage, etc., following the dosage regime described herein.

Without further elaboration, it is believed that one skilled in the art can, using the preceding description, utilize the present invention in its fullest extent. The preferred specific embodiments are, therefore, to be construed as merely illustrative, and not limitative of the disclosure in any way whatsoever.

The entire disclosure of all applications, patents and publications, cited above and below are hereby incorporated by reference.

EXAMPLES

Example 1: Treatment of Climacterium (Climacteric Symptoms)

To a nonpregnant human female (ca 45 years; 50–80 kg) displaying the signs of menopause or postmenopausal symptoms, including amenorrhea, hot flushes, etc., administer L-arginine 0.5 to 20 g of L-arginine per os daily in three divided doses until the symptoms are ameliorated. Thereafter, administer 0.5 to 5 g of L-arginine daily.

Example 2: Treatment of Climacterium (Climacteric Symptoms)

To a female comparable to and displaying the same symptoms as Example 1, administer daily 2×2.5 mg of nitroglycerine.

Example 3: Treatment of Climacterium (Climacteric Symptoms)

To a female similar to and displaying the same symptoms as Example 1, administer daily 2×2.5 mg nitroglycerin with a progestin (e.g., norgestrel) 150 mg per day.

Similarly, administer twice these dosages to a human male (100 kg) exhibiting climacterium symptoms.

Example 4: Hormone Replacement Therapy

To a female similar to and displaying the same symptoms as Example 1, administer daily 0.5 to 20 g of L-arginine in combination with estrogen (e.g., estradiol valerate) 1–2 mg daily.

Example 5: Hormone Replacement Therapy

To a female comparable to and displaying the same symptoms as Example 1, administer L-arginine 0.5 to 20 g daily and/or a nitric oxide donor (e.g., nitroglycerine, 2×2.5 mg) daily with or without one of the following, an estrogen (e.g., estradiol valerate) 1–2 mg daily, on a progestin (e.g., norgestrel, at 150 mg per day). The latter sex steroids to be given either continuously with L-arginine and/or a nitric oxide donor, or sequentially—the progestins taken for only 6–12 days per month.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating climacterium (climacteric symptoms) in a non-pregnant female mammal suffering from menopausal symptoms of climacterium, exhibiting climacteric symptoms, or who is a candidate for hormone replacement therapy, comprising administering to said female mammal an amount of nitric oxide synthase substrate, a nitric oxide donor, or both, effective to raise the blood level of circulating L-arginine to at least about 10–50 nmolar above the normally 50–100 nmolar circulating levels and, optionally, also a progestin or both of an estrogen and a progestin, in amounts effective to ameliorate the symptoms thereof.

2. The method of claim 1, wherein the mammal is a non-pregnant human female suffering from menopausal symptoms of climacterium.

3. The method of claim 1, wherein the mammal is a non-pregnant human female exhibiting climacteric symptoms or who is a candidate for hormone replacement therapy.

4. The method of claim 1, wherein the mammal is a non-pregnant female human and a nitric oxide synthase substrate is administered thereto.

5. The method of claim 4, wherein the nitric oxide substrate is L-arginine.

6. The method of claim 1, wherein the mammal is a non-pregnant human female and a nitric oxide donor is administered thereto.

7. The method of claim 6, wherein the nitric oxide donor is sodiumnitroprusside, nitroglycerin, glyceryltrinitrate, SIN-1, isosorbidmononitrate or isosorbiddinitrate.

8. The method of claim 6, wherein the nitric oxide donor is administered orally.

9. The method of claim 1, wherein the mammal is a non-pregnant human female and the nitric oxide substrate or donor is administered thereto in combination with an estrogen.

10. The method of claim 9, wherein the estrogen is estradiol valerate, conjugated equine estrogens, 17β-estradiol, estrone or estriol.

11. The method of claim 1, wherein the mammal is a non-pregnant human female and the nitric oxide substrate or donor is administered thereto in combination with a progestin.

12. The method of claim 11, wherein the progestin is progesterone, dydrogesterone, medroxyprogesterone, norethisterone, levonorgestrel or norgestrel.

13. The method of claim 1, wherein the mammal is a non-pregnant human female and concurrently a hormone replacement amount of an estrogen or a progestin is administered thereto continuously.

14. The method of claim 1 wherein the mammal is a non-pregnant human female and concurrently hormone replacement amounts of an estrogen and a progesterin is administered sequentially.

* * * * *

UNITED STATES PATENT AND TRADEMARK OFFICE
CERTIFICATE OF CORRECTION

PATENT NO. : 5,595,970
DATED : January 21, 1997
INVENTOR(S) : Robert E. Garfield et al.

It is certified that error appears in the above-identified patent and that said Letters Patent is hereby corrected as shown below:

Title Page, Item [73] Assignee:
After "Germany" insert - - and Board of Regents, University of Texas System, Austin Texas - -.

Signed and Sealed this

Twenty-ninth Day of September, 1998

Attest:

BRUCE LEHMAN

Attesting Officer

Commissioner of Patents and Trademarks